United States Patent [19]

Mathison

[11] 4,022,900

[45] * May 10, 1977

[54] COMPOSITIONS CONTAINING 1,2,3,4-TETRAHYDROISOQUINOLINES USED AS HYPOTENSIVE AGENTS

[75] Inventor: Ian William Mathison, Memphis, Tenn.

[73] Assignee: Marion Laboratories, Inc., Kansas City, Mo.

[*] Notice: The portion of the term of this patent subsequent to July 4, 1989, has been disclaimed.

[22] Filed: Dec. 11, 1972

[21] Appl. No.: 314,273

Related U.S. Application Data

[63] Continuation-in-part of Ser. No. 70,900, Sept. 9, 1970, which is a continuation-in-part of Ser. No. 715,946, March 26, 1968, Pat. No. 3,674,791.

[52] U.S. Cl. .............................................. 424/258
[51] Int. Cl.$^2$ ........................................ A61K 31/47
[58] Field of Search ................. 424/258; 260/287 R

[56] References Cited

UNITED STATES PATENTS

| 3,022,308 | 2/1962 | Cavallito | 260/286 |
| 3,674,791 | 7/1972 | Mathison | 260/287 |

FOREIGN PATENTS OR APPLICATIONS 730,509  9/1969  Belgium

OTHER PUBLICATIONS

Lusinchi et al., C.A. 53:21946–21947 (1959).
Beeby et al., C.A. 44:1510 (1956).

*Primary Examiner*—Leonard Schenkman
*Attorney, Agent, or Firm*—Merriam, Marshall, Shapiro & Klose

[57] ABSTRACT

Disclosed are 5,6,7 or 8-nuclear substituted benzamido-1,2,3,4-tetrahydroisoquinolines of the formula

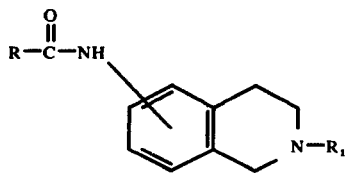

in which R is a phenyl containing one to three hydroxyl, nitro, halo, lower alkyl or lower alkoxy groups, and $R_1$ is hydrogen or a lower alkyl. The compounds lower blood pressure in animals.

10 Claims, No Drawings

COMPOSITIONS CONTAINING 1,2,3,4-TETRAHYDROISOQUINOLINES USED AS HYPOTENSIVE AGENTS

This application is a continuation-in-part of copending application Ser. No. 70,900 filed Sept. 9, 1970. Ser. No. 70,900 is a continuation-in-part of copending U.S. patent application Ser. No. 715,946 filed Mar. 26, 1968, now U.S. Pat. No. 3,674,791 issued July 4, 1972.

This invention relates to isoquinoline derivatives. More particularly, this invention is concerned with novel 5,6,7 or 8-substituted benzamido-1,2,3,4-tetrahydroisoquinolines and processes of producing such compounds as intermediates used in such processes.

According to one aspect of the present invention there are provided novel 5,6,7 or 8-substituted benzamido-1,2,3,4-tetrahydroisoquinolines of the formula

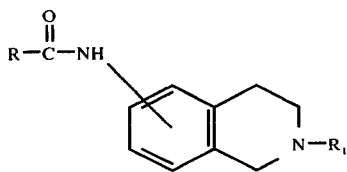

in which formula R represents substituted phenyl groups containing from one to three substitutents such as hydroxyl, nitro, halo groups including chloro, bromo, iodo, and fluoro, lower alkyl groups such as methyl and ethyl, and lower alkoxy groups such as methoxy and ethoxy, and $R_1$ represents hydrogen or a lower alkyl group such as methyl, ethyl and propyl.

The compounds described above in which $R_1$ is a lower alkyl group can be produced by reacting a nuclear substituted benzoyl halide with a 2-lower alkyl-5,6,7 or 8-amino-1,2,3,4-tetrahydroisoquinoline under suitable reaction conditions. The reaction can be represented as follows:

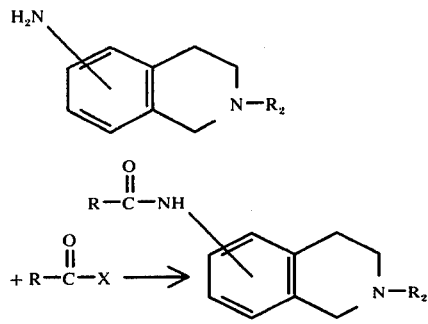

wherein R has the meaning given above, $R_2$ is a lower alkyl and X is a reactive halo group, and particularly a chloro or bromo group.

The 5,6,7 or 8-amino-1,2,3,4-tetrahydroisoquinolines used as starting materials are disclosed in the prior art. Thus, 2-methyl-8-amino-1,2,3,4-tetrahydroisoquinoline is disclosed in Chem. Pharm. Bull. (Japan) 15 (2) 168-172 (1967). 2-Methyl-6-amino-1,2,3,4-tetrahydroisoquinoline and 2-methyl-7-amino-1,2,3,4-tetrahydroisoquinoline are disclosed in Chem. Pharm. Bull. (Japan) 6 (5) 497-500 (1958). 2-methyl-5-amino-1,2,3,4-tetrahydroisoquinoline is disclosed in Chem. Pham. Bull. (Japan) 9 (6) 480-484 (1961). Homologs of such compounds containing 2-ethyl, 2-propyl or other 2-lower alkyl-5,6,7 -or 8-amino-1,2,3,4-tetrahydroisoquinoline compounds can be produced in the same way using known procedures. Thus 2-lower alkyl-5,6,7, or 8-amino-1,2,3,4-tetrahydroisoquinolines are produced by catalytically reducing a 2-lower alkyl-5,6,7, or 8-nitroisoquinolinium salt to the respective 2-lower alkyl-5,6,7 or 8-aminotetrahydroisoquinoline. This process can be represented as follows:

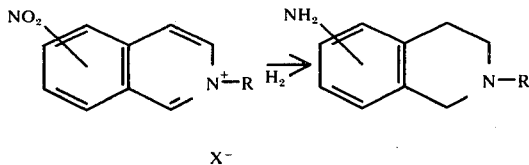

wherein R represents a lower alkyl such as methyl, ethyl and propyl, and X represents an anion such as the chloride, bromide, iodide, sulfate and p-toluenesulfonate ions.

Chem. Pharm. Bull. (Japan) 6, 497—500 (1958) discloses the 5,6 and 7-nitroisoquinolines and the 8-nitro compound is disclosed in Elderfield "Heterocyclic Compounds" Vol. IV, p. 410-411 (1952).

The 2-lower alkyl nitroisoquinolinium salts are readily obtained by quaternizing a 5,6,7 or 8-nitroisoquinoline with an appropriate alkylating agent such as an alkyl halide, alkyl sulfate or alkyl p-toluenesulfonate. Conventional procedures and conditions for the quaternizing can be used. Among the salts which can be used are 2-methyl-5-nitroisoquinolinium chloride, 2-ethyl-5-nitrosioquinolinium iodide, 2-methyl-5-nitroisoquinolinium sulfate, 2-propyl-7-nitroisoquinolinium iodide and 2-methyl-5-nitroisoquinolinium p-toluenesulfonate.

The 2-lower alkyl-5,6,7, or 8-nitroisoquinolinium salt can be catalytically hydrogenated directly to a 2-lower alkyl-5,6,7 or 8-amino-1,2,3,4-tetrahydroisquinoline. The hydrogenation can be readily effected by use of a platinum oxide catalyst in methanol and a hydrogen pressure of about 25 to 100 psi. The hydrogenation proceeds at room temperature. After filtering to remove the catalyst, the filtrate can be worked up to obtain the 2-lower alkyl-5,6,7 or 8-amino-1,2,3,4-tetrahydroisoquinoline.

Among the 2-lower alkyl-5,6,7 or 8-amino-1,2,3,4-tetrahydroisoquinolines which are produced by the described process are:
2-methyl-5-amino-1,2,3,4-tetrahydroisoquinoline,
2-ethyl-8-amino-1,2,3,4-tetrahydroisoquinoline and
2-propyl-7-amino-1,2,3,4-tetrahydroisoquinoline The nuclear-substituted benzoyl halide reactants used in making the compounds of this invention are also disclosed in the prior art. p-Methoxybenzoyl chloride (anisoyl chloride), 3,4-dimethoxybenzoyl chloride (veratryl chloride) and 3,4,5-trimethoxybenzoyl chloride (tri-o-methylgalloyl chloride) for example are disclosed in U.S. Pat. No. 3,317,541.

The reaction of the nuclear-substituted benzoyl halide and the 2-lower alkyl-5,6,7 or 8-amino-1,2,3,4-tetrahydroisoquinoline is readily effected by bringing the reactants together in an organic solvent under anhydrous conditions at moderately elevated temperatures, and advisably under reflux conditions. Dry benzene and toluene are particularly suitable reaction media. After the reaction is terminated the desired product can be isolated from the reaction mixture by conventional procedures.

Some of the benzamido compounds produced as described are:

5-(3,4,5-trimethoxybenzamido)-2-ethyl-1,2,3,4-tetrahydroisoquinoline,
6-(3,5-dimethoxybenzamido)-2-propyl-1,2,3,4-tetrahydroisoquinoline,
7-(2-bromobenzamido)-2-methyl-1,2,3,4-tetrahydroisoquinoline, and
5-(3,4,5-trimethylbenzamido)-2-ethyl-1,2,3,4-tetrahydroisoquinoline.

Acid addition salts of the tertiary bases of this invention are produced by contacting the compounds with an organic or inorganic acid such as hydrochloric sulfuric, formic, citric, maleic, succinic and fumaric acids.

Quaternary ammonium salts are formed by contacting the tertiary amines with a suitable alkylating agent such as dimethyl sulfate or an alkyl halide such as methyl chloride and ethyl bromide.

The 5,6,7 or 8-nuclear substituted benzamido-1,2,3,4-tetrahydroisoquinolines unsubstituted in the 2-position can be produced by reacting a 5,6,7 or 8-aminoisoquinoline with a nuclear-substituted benzoyl halide to produce a 5,6,7 or 8-(nuclear-substituted benzamido) isoquinoline which can then be catalytically hydrogenated to form the 5,6,7 or 8-(nuclear-substituted benzamido)-1,2,3,4-tetrahydroisoquinoline. This process can be represented as follows:

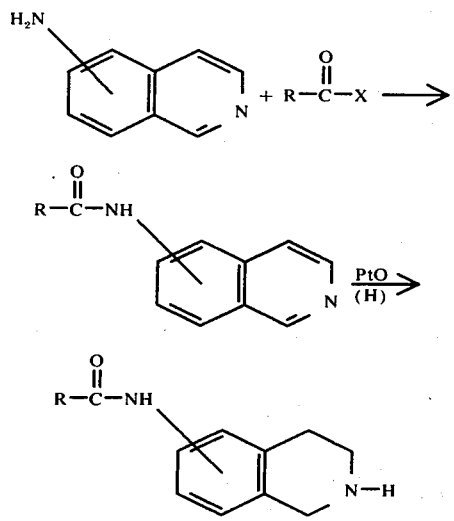

in which R and X have the assigned significance.

Chem. Pharm. Bull. (Japan) 6 (5) 497-500 (1958) disclosed 6-aminoisoquinoline and 7-aminoisoquinoline. Elderfield "Heterocyclic Compounds" Vol. IV, 411 (1952) discloses 5-aminoisoquinoline. Chem. Pharm. Bull. (Japan) 15 (2) 168–172 (1967) discloses 8-aminoisoquinoline.

Nuclear-substituted benzoyl halides such as those previously named and described can be used in the process.

Reaction between the 5,6,7 or 8 aminoisoquinoline and the nuclear-substituted benzoyl halide can be readily effected by bringing the reactants together in a suitable solvent under anhydrous conditions. The reaction proceeds at room temperature but moderately elevated temperatures can be used to enhance the reaction. After the reaction is completed, the product can be separated by conventional means.

Among the intermediate products which can be produced as described are:

5-(3,4,5-trimethoxybenzamido) isoquinoline,
6-(3,4-dimethoxybenzamido) isoquinoline,
8-(2-bromobenzamido) isoquinoline,
7-(2-fluorobenzamido) isoquinoline,
8-(4-methoxybenzamido) isoquinoline,
5-(2,6-dimethylbenzamido) isoquinoline and
6-(2-nitrobenzamido) isoquinoline.

Reduction of the 5,6,7 or 8-(nuclear-substituted benzamido) isoquinoline to the respective 5,6,7 or 8-(nuclear-substituted benzamido)-1,2,3,4-tetrahydroisoquinoline is readily effected catalytically using platinum oxide as the catalyst and methanol as the hydrogenation medium at hydrogen pressures of about 25 to 100 psi and temperatures of about 40° to 120° F. A small amount of acid, such as hydrochloric acid or sulfuric acid, can be included to facilitate the reaction. After the reduction is terminated, the catalyst can be removed by filtration and the product isolated from the filtrate by conventional procedures. The product can be separated as the free base or as an acid addition salt of acids such as previously described.

Among the 5,6,7 or 8-(nuclear-substituted benzamido)-1,2,3,4-tetrahydroisoquinolines which can be produced as described are the following:

5-(3,4,5-trimethoxybenzamido)-1,2,3,4-tetrahydroisoquinoline,
6-(3,4-dimethoxybenzamido)-1,2,3,4-tetrahydroisoquinoline, 8-(2-bromobenzamido)-1,2,3,4-tetrahydroisoquinoline,
7-(2-fluorobenzamido)-1,2,3,4-tetrahydroisoquinoline,
8-(4-methoxybenzamido)-1,2,3,4-tetrahydroisoquinoline,
5-(2,6-dimethylbenzamido)-1,2,3,4-tetrahydroisoquinoline, and
6-(2-nitroenzamido)-1,2,3,4-tetrahydroisoquinoline.

The compounds of this invention, being amines, have use as neutralizing agents. In addition, the compounds may be used in the isolation and purification of penicillin with which they will form salts.

The compounds of this invention also possess biological activity in animals and thus are potentially useful as drugs. They can be used as biologically active standards in evaluating other compounds for similar activity in animals.

In general, the compounds lower blood pressure when administered intravenously to animals although the dosage required can vary from compound to compound as can the extent of the reduction and the time it will be sustained. The compounds are thus hypotensive agents and can be administered orally to lower blood pressure.

The active agents of this invention can be administered to animals as pure compounds. It is advisable, however, to first combine one or more of the compounds with a suitable pharmaceutical carrier to attain a satisfactory size to dose relationship.

Pharmaceutical carriers which are liquid or solid can be used. Solid carriers such as starch, sugar, talc and the like can be used to form powders. The powders can be used for direct administration or they may be used to make tablets or fill gelatin capsules. Suitable lubricants like magnesium stearate, binders such as gelatin, and disintegrating agents like sodium carbonate in combination with citric acid can be used to form tablets.

Unit dosage forms such as tablets and capsules can contain any suitable predetermined amount of one or more of the active agents, and may be administered one or more at a time at regular intervals. Such unit dosage forms, however, should generally contain a concentration of 0.1 to 50% by weight of one or more of the active compounds. Unit dosages, such as tablets and capsules, can contain about 0.02 to 400 mg, and advisably 0.02 to 300 mg, of active agent.

A typical tablet can have the composition:

|  | Mg |
|---|---|
| 5-(3,4,5-trimethoxybenzamido)-2-methyl-1,2,3,4-tetrahydro-isoquinoline | 20 |
| Starch, U.S.P. | 57 |
| Lactose, U.S.P. | 73 |
| Talc, U.S.P. | 9 |
| Stearic acid | 6 |

Since many of the free bases are insoluble in water they can be suspended in sterile water by suitable means such as colloidal gums and the like to prevent settling and thereby assure uniform drug concentration per dose.

Although the oral route of administration is preferred, intravenous injection is also suitable.

The following examples are presented to illustrate preparation of novel compounds within the scope of the invention and intermediates useful in making such compounds. After the examples, data is given showing the hypotensive activity of some of the compounds provided by this invention.

EXAMPLE 1

5-Aminoisoquinoline

5-Nitroisoquinoline (16.4 g) was dissolved in methanol (200 ml) and hydrogenated over palladium on charcoal (1.64 g) at 45 psi. When the hydrogenation was complete, the catalyst was removed by filtration and the solvent removed in vacuo to yield 15.2 g of 5-aminoisoquinoline as a brown powder. This was recrystallized from chloroform-ligroin (b.p. 60°–90° C.) to yield 5-aminoisoquinoline (12.1 g) as a light tan powder, m.p. 127°–129° C. (lit. value, 128° C.).

In the same way, 6-nitroisoquinoline is reduced to 6-aminoisoquinoline; 7-nitroisoquinoline is reduced to 7-aminoisoquinoline; and 8-nitroisoquinoline is reduced to 8-aminoisoquinoline.

EXAMPLE 2

5-Nitro-2-methylisoquinolinium p-toluenesulfonate

5-Nitroisoquinoline (25 g) and methyl p-toluenesulfonate (26.8 g) were dissolved in dimethylformamide (80 ml) and allowed to stand at room temperature for three days. If a crystalline cake had not formed at the end of this time, the solution was either seeded or scratched to initiate precipitation of the product. The supernatant was decanted and ethyl acetate was added to this until no more precipitation was evident. This precipitate was collected by filtration and combined with the first precipitate. The product was recrystallized from ethanol-ethyl acetate to yield 43.9 g of yellow crystals, m.p. 144°–144.7°C.

Anal. Calcd. for $C_{17}H_{16}N_2O_5S$: C, 56.65; H, 4.48; N 7.78; S, 8.90. Found: C, 56.58; H, 4.62; N, 7.92; S, 8.98.

EXAMPLE 3

5-Nitro-2-n-propylisoquinolinium bromide

5-Nitroisoquinoline (10.0 g) and 1-bromopropane (7.8 g) were refluxed in ethanol (200 ml) for 5 days. On cooling to room temperature, a yellow powdery precipitate formed. This was collected by vacuum filtration and purified by recrystallization from ethanol to yield 8.2 g of the desired 5-nitor-2-n-propylisoquinolinium bromide as yellow, crystalline needles, m.p. 206.5°–209.5° C.

Anal. Calcd. for $C_{12}H_{13}N_2O_2Br$: C, 48.50; H, 4.41; N, 9.43; Br, 26.89.

Found: C, 48.31; H, 4.26; N, 9.35; Br, 27.06.

EXAMPLE 4

5-Amino-2-methyl-1,2,3,4-tetrahydroisoquinoline

5-Nitro-2-methylisoquinolinium p-toluenesulfonate (37 g) was dissolved in methanol (150 ml) and was hydrogenated over platinum oxide (0.6 g) at 45 psi. When hydrogen uptake was complete, the catalyst was removed by filtration and the solvent was removed in vacuo leaving a viscous yellow oil. The oil was dissolved in water and made strongly alkaline with sodium hydroxide pellets. This solution was extracted with chloroform and the chloroform dried over anhydrous sodium sulfate. The chloroform was distilled off to yield 16.6 g of 5-amino-2-methyl-1,2,3,4-tetrahydroisoquinoline as a red oil.

EXAMPLE 5

5-Amino-2-n-propyl-1,2,3,4-tetrahydroisoquinoline HBr

5-Nitro-2-n-propylisoquinolinium bromide (8.2 g) was dissolved in methanol (150 ml) and the solution hydrogenated over platinum oxide (0.6 g) at 45 psi. When the hydrogenation was complete, the catalyst was removed by filtration and the solvent removed in vacuo to leave a light orange solid residue of 5-amino-2-n-propyl-1,2,3,4-tetrahydroisoquinoline hydrobromide (7.5 g). This residue was recrystallized from ethanol and the product obtained as pale orange crystals, m.p. 238°–239.5° C.

EXAMPLE 6

3,4-Dimethoxybenzoyl chloride

Veratric acid (3,4-dimethoxybenzoic acid) (25 g) was suspended in dry benzene (400 ml) and treated with a large excess of thionyl chloride. This mixture was refluxed for 5 hours. The benzene was removed in vacuo and the oily residue was washed 5 times with 150 ml portions of fresh dry benzene followed by distillation of the benzene to remove excess thionyl chloride. This yielded 26.5 g of the desired acid chloride as a light brown solid, m.p. 68°–69° C. (lit. value, 70° C.).

EXAMPLE 7

O-Fluorobenzoyl chloride o-Fluorobenzoic acid (10 g) was suspended in dry benzene (200 ml) and treated with a large excess of thionyl chloride. This solution was refluxed for 4 hours. The benzene was removed in vacuo leaving a yellow oil. This oil was washed 5 times with 150 ml portions of fresh dry benzene followed by distillation of the benzene to remove excess thionyl chloride. This yielded 10.5 g of the acid chloride as a yellow oil (lit. value m.p. 4° C.).

The following acid chlorides are some of those similarly prepared: anisoyl chloride, 3,4,5-trimethoxybenzoyl chloride, 2,6-dimethoxybenzoyl chloride, 2,4,5-trimethoxybenzoyl chloride, 2,6-dimethylbenzoyl chloride, 2,6-diethylbenzoyl chloride and o-nitrobenzoyl chloride.

EXAMPLE 8

5-(3,4-Dimethoxybenzamido)-1,2,3,4-tetrahydroisoquinoline HCl (M-34)

5-Aminoisoquinoline (8 g.) was dissolved in dry benzene (100 ml) and 0.5 g of dry potassium bicarbonate was added to the solution. A 0.1 mole excess of 3,4-dimethoxybenzoyl chloride was dissolved in dry benzene (50 ml) and this solution was poured into the solution of 5-aminoisoquinoline. A precipitate formed immediately. This was collected by filtration and washed with 10% sodium carbonate solution followed by water. The washings were discarded and the insoluble residue was recrystallized from benzene to yield 11.5 g of 5-(3,4-dimethoxybenzamido)isoquinoline as tan needles, m.p. 193°–194° C.

Anal. Calcd. for $C_{18}H_{16}N_2O_3$: C, 70.12; H, 5.23; N, 9.08. Found: C, 70.32; H, 5.41; N, 9.03.

5-(3,4-dimethoxybenzamido) isoquinoline (2.7 g) was dissolved in 10% hydrochloric acid (100 ml) and methanol (100 ml) with warming. This was hydrogenated over platinum oxide (200 mg) at 45 psi. The catalyst was removed by filtration and the filtrate cooled in the refrigerator. A white precipitate formed and was collected by filtration and recrystallized from methanol to yield 2.1 g of 5-(3,4-dimethoxybenzamido)-1,2,3,4-tetrahydroisoquinoline hydrochloride as a white crystalline powder, m.p., 287°–288° C.

Anal. Calcd. for $C_{18}H_{21}N_2O_3Cl$: C, 61.97; H, 6.07; N, 8.03; Cl, 10.16. Found: C, 61.73, H, 6.25; N, 7.89; Cl, 10.31.

EXAMPLE 9

5-(4-Methoxybenzamido)-1,2,3,4-tetrahydroisoquinoline HCl (M-44)

Anisoyl chloride was reacted with 5-aminoisoquinoline according to the procedure of Example 8 to produce 5-(4-methoxybenzamido) isoquinoline. This product was then reduced according to the procedure of Example 8 to yield 5-(4-methoxybenzamido)-1,2,3,4-tetrahydroisoquinoline HCl. After purification from water it had a melting point of 289°–290° C.

Anal. Calcd. for $C_{17}H_{19}N_2O_2Cl$: C, 64.04; H, 6.01; N, 8.79; Cl, 11.12. Found: C, 64.34; H, 6.11; N, 8.69; Cl, 11.21.

EXAMPLE 10

5-(3,4,5-Trimethoxybenzamido)-1,2,3,4-tetrahydroisoquinoline HCl (M-46)

3,4,5-Trimethoxybenzoyl chloride was reacted with 5-aminoisoquinoline according to the procedure of Example 8 to produce 5-(3,4,5-trimethoxybenzamido) isoquinoline. This product was then reduced according to the procedure of Example 8 to yield 5-(3,4,5-trimethoxybenzamido)-1,2,3,4-tetrahydroisoquinoline HCl. After purification from methanol it had a melting point of 270°–271.5° C.

Anal. Calcd. for $C_{19}H_{23}N_2O_4Cl$; C, 60.23; H, 6.12; N, 7.39; Cl, 9.36. Found: C, 60.26; H, 6.09; N, 7.22; Cl, 9.55.

EXAMPLE 11

5-(3,4,5-Trimethoxybenzamido)-2-methyl-1,2,3,4-tetrahydroisoquinoline (M-20)

5-Amino-2-methyl-1,2,3,4-tetrahydroisoquinoline (3.76 g) was dissolved in anhydrous benzene (100 ml) and treated with 3,4,5-trimethoxybenzoyl chloride (5 g) under reflux for 16 hours in the presence of 0.25 g of anhydrous potassium bicarbonate. The precipitated solid was filtered and washed with sodium carbonate solution. The solid was recrystallized from benzene to yield 4.04 g of fine needles; mp 142.8-143.1° C.

Anal. Calcd. for $C_{20}H_{24}N_2O_4$: C, 67.40; H, 6.79; N, 7.86 Found: C, 67.24; H, 6.64; N, 7.76.

EXAMPLE 12

5-(3,4-Dimethyoxybenzamido)-2-methyl-1,2,3,4-tetrahydroisoquinoline (M-55)

5-Amino-2-methyl-1,2,3,4-tetrahydroisoquinoline (12.9 g) prepared as in Example 4 was dissolved in dry benzene (100 ml) and 0.5 g of dry potassium bicarbonate was added. A 0.1 mole excess of 3,4-dimethoxybenzoyl chloride was dissolved in dry benzene (100 ml) and this solution was added to the solution of the tetrahydroisoquinoline. A precipitate formed immediately and the mixture was refluxed for 1 hour. The precipitate was collected by filtration and washed with 10% sodium carbonate solution followed by water. The washings were discarded and the remaining residue was recrystallized from ethanol to yield 12.0 g of the desired product as a white powder, m.p. 160°–161.5° C.

Anal. Calcd. for $C_{19}H_{22}N_2O_3$: C, 69.91; H, 6.79; N, 8.58. Found: C, 69.84; H, 6.84; N, 8.50

EXAMPLE 13

5-(3,4,5-Trimethoxybenzamido)-2-n-propyl-1,2,3,4-tetrahydroisoquinoline (M-49)

5-Amino-2-n-propyl-1,2,3,4-tetrahydroisoquinoline hydrobromide (13.7 g) prepared as in Example 5 was suspended in dry benzene (100 ml) and 0.5 g of dry potassium bicarbonate was added. A 0.1 mole excess of 3,4,5-trimethoxybenzoyl chloride was dissolved in dry benzene (100 ml) and this solution was added to the solution of the tetrahydroisoquinoline. The mixture was refluxed for 5 days. The precipitate formed was collected by filtration and washed with 10% sodium carbonate solution followed by water. The washings were discarded and the remaining solid (11.7 g) was purified by recrystallization from ethanol to yield 5-(3,4,5-trimethoxybenzamido)-2-n-propyl-1,2,3,4-tetrahydroisoquinoline as a white powder, m.p., 158.5°–159.5° C.

Anal. Calcd. for $C_{22}H_{28}N_2O_4$: C, 68.72; H, 7.34; N, 7.29. Found: C, 68.66; H, 7.20; N, 7.42.

EXAMPLE 14

5-(3,4-Dimethoxybenzamido)-2-n-propyl-1,2,3,4-tetrahydroisoquinoline (M-47)

5-Amino-2-n-propyl-1,2,3,4-tetrahydroisoquinoline hydrobromide (10 g) prepared as in Example 5 was suspended in dry benzene (100 ml) and 0.5 g dry potassium bicarbonate was added. A 0.1 mole excess of 3,4-dimethoxybenzoyl chloride was dissolved in dry benzene (100 ml) and this solution was added to the solution of the tetrahydroisoquinoline. The mixture was refluxed for 5 days. The precipitate formed at the end of this period was collected by filtration and washed with 10% sodium carbonate solution followed by water. The washings were discarded and the remaining solid was purified by recrystallization from ethanol to yield 6.7 g of 5-(3,4-dimethoxybenzamido)-2-n-propyl-1,2,3,4-tetrahydroisoquinoline as a white powder, m.p. 146°–147° C.

Anal. Calcd. for $C_{21}H_{26}N_2O_3$: C, 71.16; H, 7.39; N, 7.90. Found: C, 70.95; H, 7.17; N, 7.85.

EXAMPLE 15

8-(3,4,5-Trimethoxybenzamido)-2-methyl-1,2,3,4-tetrahydroisoquinoline (M-65)

8-Amino-2-methyl-1,2,3,4-tetrahydroisoquinoline (2 g) prepared from 8-nitro-2-methyl-isoquinolinium p-toluenesulfonate as described for the 5-nitro isomer in Example 4 was dissolved in dry benzene (100 ml) and 0.5 g of dry potassium bicarbonate was added. A 0.1 mole excess of 3,4,5-trimethoxybenzoyl chloride was dissolved in dry benzene (50 ml) and this solution was added to the solution of the tetrahydroisoquinoline. The solutions clouded on mixing and were then refluxed for 12 hours. After refluxing, the benzene was removed in vacuo leaving a viscous, yellow oil. This was suspended in 10% sodium carbonate solution to remove excess acid chloride. The insoluble oil was extracted from the aqueous sodium carbonate with chloroform which was dried over anhydrous magnesium sulfate. The chloroform was distilled off to leave a viscous, yellow oil. This was washed with ether and a white solid (3 g) formed. This was recrystallized from ethanol-water to yield the desired product as white felted needles, m.p. 177°–178.3° C.

Anal. Calcd. for $C_{20}H_{24}N_2O_4$: C, 67.40; H, 6.79; N, 7.86. Found: C, 67.50; H, 6.78; N, 7.96.

EXAMPLE 16

7-(3,4,5-Trimethoxybenzamido)-2-methyl-1,2,3,4-tetrahydroisoquinoline (M-59)

7-Amino-2-methyl-1,2,3,4-tetrahydroisoquinoline (2 g), prepared from 7-nitro-2-methyl-isoquinolinium p-toluenesulfonate as described for the 5-nitro isomer in Example 4 was dissolved in dry benzene (50 ml) and 0.5 g of dry potassium bicarbonate was added. A 0.1 mole excess of 3,4,5-trimethoxybenzoyl chloride was dissolved in benzene (50 ml) and this solution was added to the solution of the tetrahydroisoquinoline. A brown precipitate formed immediately and the mixture was refluxed for 3 hours. The benzene was removed in vacuo leaving a tan residue which was suspended in 10% sodium carbonate solution to remove excess acid chloride and stirred for 1 hour. The insoluble residue was a brown oil which was extracted from the aqueous sodium carbonate with chloroform. The chloroform was dried over anhydrous magnesium sulfate and the chloroform was distilled off to leave a viscous red oil which crystallized to a white powder (2.7 g) when washed with cold ether. The white solid was recrystallized from ethanol-ether to yield the desired product as a white powder, m.p. 157.5°–158° C.

Anal. Calcd. for $C_{20}H_{24}N_2O_4$: C, 67.40; H, 6.79; N, 7.86. Found: C, 67,42; H, 6.69; N, 7.75

EXAMPLE 17

6-(3,4,5-Trimethoxybenzamido)-2-methyl-1,2,3,4-tetrahydroisoquinoline HCl (M-72)

6-Amino-2-methyl-1,2,3,4-tetrahydroisoquinoline was reacted with 3,4,5-trimethoxybenzoyl chloride as in Example 16 to yield 6-(3,4,5-trimethoxybenzamido)-2-methyl-1,2,3,4-tetrahydroisoquinoline. It was recovered as the HCl salt; m.p. 233.5°–235° C. after purification in methanol.

Anal. Calcd. for $C_{20}H_{25}N_2O_4Cl$:C, 61.14; H, 6.42; N, 7.13; Cl, 9.03. Found: C, 61.30; H, 6.49; N, 7.26; Cl, 9.28.

EXAMPLE 18

5-(2-Chlorobenzamido)-2-methyl-1,2,3,4-tetrahydroisoquinoline (M-63)

5-Amino-2-methyl-1,2,3,4-tetrahydroisoquinoline (9.2 g) prepared as in Example 4 was dissolved in dry benzene (100 ml) and 0.5 g of dry potassium bicarbonate was added. A 0.1 mole excess of 2-chlorobenzoyl chloride was dissolved in dry benzene (100 ml) and this solution was added to the solution of the tetrahydroisoquinoline. A white precipitate formed immediately and the mixture was then refluxed for 1 hour. The precipitate was collected by filtration and was washed with 10% sodium carbonate solution followed by water. The washings were discarded and the remaining residue was recrystallized from ethanol to yield 12.6 g of the desired product as fluffy, crystalline plates, m.p., 189.5°–191.5° C.

Anal. Calcd. for $C_{17}H_{17}N_2OCl$: C, 67.88; H, 5.70; N, 9.31; Cl, 11.79. Found: C, 67.69; H, 5.65; N, 9.19; Cl, 11.92.

EXAMPLE 19

5-(2-Fluorobenzamido)-2-methyl-1,2,3,4-tetrahydroisoquinoline (M-68)

5-Amino-2-methyl-1,2,3,4-tetrahydroisoquinoline (5.0 g) prepared as in Example 4 was dissolved in dry benzene (75 ml) and 0.5 g of dry potassium bicarbonate was added. A 0.1 mole excess of 2-fluorobenzoyl chloride was dissolved in dry benzene (75 ml) and this solution was added to the solution of the tetrahydroisoquinoline. A white precipitate formed immediately. The mixture was refluxed for 1 hour to insure that the reaction had gone to completion. The precipitate was collected by vacuum filtration and washed with 10% sodium carbonate solution followed by water. The washings were discarded and the remaining residue was recrystallized from ethyl acetate to yield 6.8 g of the desired product as white crystals, m.p. 112°–112.5° C.

Anal. Calcd. for $C_{17}H_{17}N_2FO$: C, 71.81; H, 6.03; N, 9.85; F, 6.68. Found: C, 72.07; H, 6.03; N, 9.87; F, 6.57.

EXAMPLE 20

5-(4-Methoxybenzamido)-2-methyl-1,2,3,4-tetrahydroisoquinoline (M-56)

5-Amino-2-methyl-1,2,3,4-tetrahydroisoquinoline was reacted with 4-methoxybenzoyl chloride according to the procedure of Example 19 to yield 5-(4-methoxybenzamido)2-methul-1,2,3,4-tetrahydroisoquinoline; m.p. 169.5°–171.5° C. after purification from ethanol.

Anal. Calcd. for $C_{18}H_{20}N_2O_2$: C, 72.94; H, 6.80; N, 9.45. Found: C, 73.09; H, 6.69; N, 9.45.

EXAMPLE 21

5-(2,6-Dimethoxybenzamido)-2-methyl-1,2,3,4-tetrahydroisoquinoline (M-57)

5-Amino-2-methyl-1,2,3,4-tetrahydroisoquinoline was reacted with 2,6-dimethoxybenzoyl chloride according to the procedure of Example 19 to yield 5-(2,6-dimethoxybenzamido)-2-methyl-1,2,3,4-tetrahydroisoquinoline; m.p. 191–192° C. after recrystallization from benzene.

Anal. Calcd. for $C_{19}H_{22}N_2O_3$: C, 69.91; H, 6.79; N, 8.58. Found: C, 69.79; H, 6.94; N, 8.53.

EXAMPLE 22

5-(2,6-Dimethoxybenzamido)-2-methyl-1,2,3,4-tetrahydroisoquinoline (M-61)

5-Amino-2-methyl-1,2,3,4-tetrahydroisoquinoline was reacted with 2,4,5-trimethoxybenzoyl chloride according to the procedure of Example 19 to yield 5-(2,4,5-trimethoxybenzamido)-2-methyl-1,2,3,4-tetrahydroisoquinoline; m.p. 159°–160.5° C. after purification from ethanol.

Anal. Calcd. for $C_{20}H_{24}N_2O_4$: C, 67.39; H, 6.79; N, 7.86. Found: C, 67.18; H, 6.87; N, 7.86.

EXAMPLE 23

5-(2,6-Dimethylbenzamido)-2-methyl-1,2,3,4-tetrahydroisoquinoline (M-58)

5-Amino-2-methyl-1,2,3,4-tetrahydroisoquinoline was reacted with 2,6-dimethylbenzoyl chloride according to the procedure of Example 19 to yield 5-(2,6-dimethylbenzamido)-2-methyl-1,2,3,4-tetrahydroisoquinoline; m.p. 199.5°–201° C. after purification from ethanol.

Anal. Calcd for $C_{19}H_{22}N_2O$: C, 77.51; H, 7.53; N, 9.52. Found: C, 77.35; H, 7.34; N, 9.41.

EXAMPLE 24

5-(2,6-Diethylbenzamido)-2-methyl-1,2,3,4-tetrahydroisoquinoline (M-66)

5-Amino-2-methyl-1,2,3,4-tetrahydroisoquinoline was reacted with 2,6-diethylbenzoyl chloride according to the procedure of Example 19 to yield 5-(2,6-diethylbenzamido)-2-methyl-1,2,3,4-tetrahydroisoquinoline; m.p. 185.5°–187.5° C. after purification from ethanol.

Anal. Calcd. for $C_{21}H_{26}N_2O$: C, 78.22; H, 8.13; N, 8.69. Found: C, 78.04; H, 8.29; N, 8.52.

EXAMPLE 25

5-(2-Nitrobenzamido)-2-methyl-1,2,3,4-tetrahydroisoquinoline (M-69)

5-Amino-2-methyl-1,2,3,4-tetrahydroisoquinoline was reacted with 2-nitrobenzoyl chloride according to the procedure of Example 19 to yield 5-(2-nitrobenzamido)-2-methyl-1,2,3,4-tetrahydroisoquinoline; m.p. 196.5°–198° C. after purification from ethanol.

Anal. Calcd. for $C_{17}H_{17}O_3N_3$: C, 65.88; H, 5.50; N, 13.50. Found: C, 65.67; H, 5.42; N, 13.74.

EXAMPLE 26

5-(2-Iodobenzamido)-2-methyl-1,2,3,4-tetrahydroisoquinoline (M-70)

5-Amino-2-methyl-1,2,3,4-tetrahydroisoquinoline was reacted with 2-isdobenzoyl chloride according to the procedure of Example 19 to yield 5-(2-iodobenzamido)-2-methyl-1,2,3,4-tetrahydroisoquinoline; m.p. 215°–216.5° C. after purification from methanol.

Anal, Calcd. for $C_{17}H_{17}N_2IO$: C, 52.06; H, 4.37; N, 7.14. Found: C, 52.28; H, 4.34; N, 7.14. Found: C, 52.28; H, 4.34; N, 7.14.

EXAMPLE 27

5-(2-Bromobenzamido)-2-methyl-1,2,3,4-tetrahydroisoquinoline (M-60)

5-Amino-2-methyl-1,2,3,4-tetrahydroisoquinoline was reacted with 2-bromobenzoyl chloride according to the procedure of Example 19 to yield 5-(2-bromobenzamido)-2-methyl-1,2,3,4-tetrahydroisoquinoline; m.p. 206.5°–208.5° C. after purification from ethanol.

Anal. Calcd. for $C_{17}H_{17}N_2BrO$: C, 59.14; H, 4.96; N, 8.11. Found: C, 58.91; H, 5.12; N, 7.98.

EXAMPLE 28

5-(4-methoxybenzamido-2-n-propyl-1,2,3,4-tetrahydroisoquinoline (M-50)

5-Amino-2-n-propyl-1,2,3,4-tetrahydroisoquinoline hydrobromide was reacted with 4-methoxybenzoyl chloride according to the procedure of Example 14 to produce 5-(4-methoxybenzamido)-2-n-propyl-1,2,3,4-tetrahydroisoquinoline; m.p. 162.5°–163.5° C. after purification with ethanol.

Anal. Calcd. for: $C_{20}H_{24}N_2O_2$: C, 74.04; H, 7/46; N, 8.63. Found: C, 74.13; H, 7.56; N, 8.63

Compounds of this invention have been studied for hypotensive properties in a hypertensive rat colony and have been shown to be active as blood pressure lowering agents. Hypertension was produced in weanling (30-day old) male rats of the CD strain obtained from the Charles River Breeding Laboratories (Wilmington, Mass.) by subcutaneously implanting about the dorsal surface of the neck a pellet of deoxycorticosterone acetate (DCA) containing 10 mg DCA in a mixture of Carbowax 4000 (Union Carbide) and Flexowax C light (Glyco Products). Their drinking water was replaced by a 1% sodium chloride solution, a procedure known to facilitate the development of an experimental hypertension, and they had free access to chow. Systolic blood pressure in the caudal arteries was measured indirectly by a pneumatic pulse transducer and a tail pressure cuff on a Physiograph Four recorder (Narco Bio-Systems, Inc., Houston, Texas) in unanesthetized but restrained rats prewarmed to 40° C, 10–15 minutes prior to the determination. The rats were kept at a temperature of 40° C. for all determinations of systolic pressure in an attempt to minimize variations in blood pressure due to marked changes in arterial tone caused by changes in temperature. Blood pressures were measured at intervals in the DCA-treated rats given saline and in non-treated control rats. After 20 days, the mean systolic pressure in the DCA-treated rats was above 150 mm Hg. Hypertension was regarded as being established in the rats at this stage and they were at intervals, usually beginning with the 30th day after DCA-implant in testing for hypotensive activity. Following a series of control blood pressure readings, a dose of 50 mg/kg of the compound under investigation was administered by intraperitoneal injection either in solution or as a suspension in 1% tragacanth solution to groups of six hypertensive rats. Blood pressures were redetermined at 1, 2, 4 and 24 hour periods following injection. At each interval, the systolic pressure was measured a minimum of five times in each rat and the average value was calculated. Mean values for the group were calculated from the individual average values and compared with their predrug control levels. The statistical significance of the changes produced by the compounds, in the doses employed, was tested by the $t$ test as well as by an analysis of variance. The reductions in blood pressure obtained with the indicated representative tetrahydroisoquinoline compounds are shown in Table I. The code number for the compound and the example herein showing its preparation are both given in Table I.

Table II

Approximate Acute Toxicity (24 hrs.) In the Mouse

| Compound Example Number | Code Number | Number of Mice Dosed | $LD_{50}$ mg/kg, i.p |
|---|---|---|---|
| 9 | M-44 | 14 | 500–1000 (a) |
| 17 | M-72 | 20 | 188–250 (b) |
| 23 | M-58 | 15 | 125–250 (c) |
| 24 | M-66 | 15 | 125–250 (c) |
| 25 | M-69 | 13 | 125–250 (c) |
| 26 | M-70 | 27 | < 31 (c) |
| 28 | M-50 | 9 | 125–250 (c) |

(a) Suspension in 1% tragacanth
(b) Solution in distilled water
(c) Solubilized with the aid of dilute acid Table I

| Compound Example No. | Compound Code No. | $LD_{50}$ | Lowering of Blood Pressure in Hypertensive rats in mm's of Hg. | | | |
|---|---|---|---|---|---|---|
| | | | 1 hr. | 2 hrs. | 4 hrs. | 24 hrs. |
| 8 | M-34 | 500–1000 | −33±5 | −28±7 | −23±4 | −2±6 |
| 10 | M-46 | 250–500 | −26±10 | −25±7 | −11±4 | −18±4 |
| 11 | M-20 | 125–250 | −19±3 | −26±2 | −15±10 | −3±2 |
| 12 | M-55 | 125–250 | −32±5 | −31±5 | −32±4 | −20±4 |
| 13 | M-49 | 125–250 | −31±6 | −27±6 | −21±6 | −17±6 |
| 14 | M-47 | 250–500 | −35±7 | −46±11 | −41±8 | −22±4 |
| 15 | M-65 | 250–500 | −55±10 | −44±8 | −27±3 | −21±7 |
| 16 | M-59 | 250–500 | −60±7 | −46±7 | −34±6 | −18±7 |
| 18 | M-63 | 125–188 | −25±2 | −36±4 | −34±4 | −28±4 |
| 19 | M-68 | 250–500 | −13±5 | −10±5 | −11±4 | −20±4 |
| 20 | M-56 | 62–125 | −14±5 | −30±8 | −19±6 | −18±4 |
| 21 | M-57 | 250–500 | −2±8 | −7±5 | −14±10 | −14±10 |
| 22 | M-61 | 68–125 | −15±4 | −19±5 | −15±4 | −6±6 |
| 27 | M-60 | 125–250 | −12±4 | −10±8 | −20±3 | −26±4 |
| None (1) | M-54 | 125–250 | −7±7 | −14±6 | −15±6 | −10±3 |

(1) 5-(benzamido)-2-methyl-1,2,3,4-tetrahydroisoquinoline. From Table I the compounds which appear most active are M-34, M-55, M-49, M-47, M-65, M-59 and M-63.

Table III

Percent Change In Systolic Blood Pressure of Unanesthetized Male Deoxycorticosterone Acetate Hypertensive Rats

| Compound Example Number | Code Number | Dose mg/kg,i.p. | No. of Rats | Control[a] | Percent Change in Pressure from Control ± S.E. | | | |
|---|---|---|---|---|---|---|---|---|
| | | | | | 1 Hour | 2 Hours | 4 Hours | 24 Hours |
| 9 | M-44 | 50 | 6 | 221 ± 10 | −8.8 ± 4.8 | −6.5 ± 3.7 | −8.3 ± 2.4 | −6.4 ± 1.3 |
| 17 | M-72 | 50 | 6 | 188 ± 7 | −21.6 ± 1.7* | −19.4 ± 4.0* | −11.9 ± 3.4* | −3.8 ± 1.3* |
| 23 | M-58 | 50 | 6 | 181 ± 8 | −6.1 ± 1.7* | −2.4 ± 0.6 | −5.2 ± 1.8* | +2.0 ± 2.1 |
| 24 | M-66 | 50 | 6 | 192 ± 3 | −5.7 ± 3.0 | −7.5 ± 4.6 | −6.1 ± 2.8 | −2.1 ± 2.3 |
| 25 | M-69 | 50 | 6 | 198 ± 7 | −6.1 ± 1.7 | −4.1 ± 3.0 | −3.3 ± 4.0 | −1.0 ± 3.0 |
| 26 | M-70 | 50 | 6 | 175 ± 3 | −6.8 ± 2.1* | −9.9 ± 2.1* | −5.7 ± 1.9* | −0.7 ± 2.9 |
| 28 | M-50 | 50 | 12 | 210 ± 10 | −11.3 ± 1.9* | −17.8 ± 1.4* | −10.2 ± 2.8* | −6.2 ± 2.0* |

[a]Mean systolic blood pressure (mm Hg) ±S.E.
* <0.05 level of significance by Newman-Keuls a posteriori test 5(3,4,5-trimethoxybenzamido)-2-methyl-1,2,3,4-tetrahydroisoquinoline (M-20) in mice has an LD-50 of about 125 to 250 mg/kg intraperitoneally. In the anesthetized dog, it is decreased arterial blood pressure at a test dose of 5 mg/kg administered intravenously. When administered into the femoral artery of a dog it was found to have peripheral vasodilator activity although less than that of papaverine.

Additional compounds have been tested. The toxicity data for the additional compounds tested, and their identity, is given in the following Table II while the blood pressure lowering activity of the compounds is given in the following Table III. The heading "Example Number" in the tables refers to the working example herein which discloses the compounds and its preparation. The test procedure used for determining the blood pressure lowering activity of the compounds is the same as that previously set forth herein. However, the figures in Table III are expressed as percentage change in blood pressure, rather than in mm of mercury change in blood pressure, as presented in Table I herein.

The foregoing detail description has been given for clearness of understanding only, and no unnecessary limitations should be understood therefrom as modifications will be obvious to those skilled in the art.

What is claimed is:

1. A method of lowering blood pressure in a hypertensive animal which comprises administering to said animal, in an amount effective to lower the blood pressure, a compound of the formula

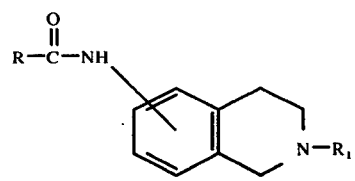

or a nontoxic acid addition salt thereof, wherein R is a nuclear substituted phenyl group containing one to three lower alkoxy groups and $R_1$ represents a lower alkyl group.

2. The method of claim 1 in which each lower alkoxy is methoxy.

3. The method of claim 2 in which $R_1$ is methyl.

4. The method of claim 2 in which $R_1$ is propyl.

5. A method of lowering blood pressure in a hypertensive animal which comprises administering to said animal, in an amount effective to lower the blood pressure, the compound 5-(3,4,5-trimethoxybenzamido)-2-methyl-1,2,3,4-tetrahydroisoquinoline.

6. An anti-hypertensive pharmaceutical composition in unit dosage form comprising about 0.02 to 400 mg of a compound of the formula

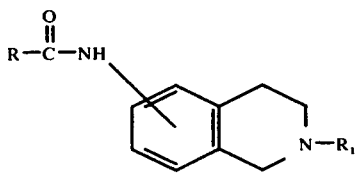

or a nontoxic acid addition salt thereof, wherein R is a nuclear-substituted phenyl group containing one to three lower alkoxy groups and $R_1$ is lower alkyl group, in admixture with a pharmaceutical carrier.

7. An anti-hypertensive composition according to claim 6 in which each alkoxy is a methoxy group.

8. An anti-hypertensive composition according to claim 7 in which $R_1$ is methyl.

9. An anti-hypertensive composition according to claim 7 in which $R_1$ is propyl.

10. An anti-hypertensive pharmaceutical composition in unit dosage form comprising about 0.02 to 400 mg of 5(3,4,5-trimethoxybenzamido)-2-methyl-1,2,3,4-tetrahydroisoquinoline in admixture with a pharmaceutical carrier.

* * * * *

UNITED STATES PATENT AND TRADEMARK OFFICE
CERTIFICATE OF CORRECTION

PATENT NO. : 4,022,900
DATED : May 10, 1977
INVENTOR(S) : Ian W. Mathison

It is certified that error appears in the above-identified patent and that said Letters Patent are hereby corrected as shown below:

Column 4, line 40, "6-(2-nitroenzamido)-" should be -- 6-(2-nitrobenzamido)- --; column 6, line 13, "5-nitor-" should be -- 5-nitro- --; column 9, line 68, "67,32" should be --67.32--; column 10, line 67, "2-methul-" should be -- 2-methyl- --; column 11, line 18, "5-(2,6-Dimethoxybenzamido)-" should be -- 5-(2,4,5-Trimethoxybenzamido)- --; column 12, line 4, "N$_2$10" should be --N$_2$IO--; line 31, "H, 7/46;" should be --H, 7.46;--; column 13, line 49, "5(3,4,5-trimethoxybenzamido)" should be -- 5-(3,4,5-trimethoxybenzamido) --; column 16, line 13, "5(3,4,5-trimethoxybenzamido)" should be -- 5-(3,4,5-trimethoxybenzamido)--.

Signed and Sealed this ninth Day of August 1977

[SEAL]

Attest:

RUTH C. MASON
*Attesting Officer*

C. MARSHALL DANN
*Commissioner of Patents and Trademarks*